United States Patent [19]

Okada

[11] Patent Number: 5,219,327
[45] Date of Patent: Jun. 15, 1993

[54] TRANSFUSION PUMP

[75] Inventor: Shigeru Okada, Fujinomoya, Japan

[73] Assignee: Terumo Kabushiki Kaisha, Tokyo, Japan

[21] Appl. No.: 782,985

[22] Filed: Oct. 28, 1991

[30] Foreign Application Priority Data

Oct. 31, 1990 [JP] Japan .................. 2-291883

[51] Int. Cl.⁵ .......................................... A61M 5/152
[52] U.S. Cl. ...................... 604/34; 604/151;
604/153; 604/250; 417/474; 251/7; 251/9;
128/DIG. 12
[58] Field of Search ............... 604/151, 153, 250, 34;
128/DIG. 12, DIG. 13; 251/7, 9; 417/474

[56] References Cited

U.S. PATENT DOCUMENTS

| | | | |
|---|---|---|---|
| 4,425,116 | 1/1984 | Bilstad et al. | 251/7 X |
| 4,460,358 | 7/1984 | Somerville et al. | 604/250 |
| 4,585,442 | 4/1986 | Mannes | 604/250 |
| 4,586,691 | 5/1986 | Kozlow | 604/250 X |
| 4,616,801 | 10/1986 | Cewers et al. | 604/250 X |
| 4,689,043 | 8/1987 | Bisha | 128/DIG. 13 X |
| 4,714,463 | 12/1987 | Archibald et al. | 604/250 X |
| 4,919,649 | 4/1990 | Timothy et al. | 604/250 X |
| 5,017,192 | 5/1991 | Dodge et al. | 604/250 |
| 5,090,877 | 2/1992 | D'Silva | 604/153 X |

FOREIGN PATENT DOCUMENTS

| | | |
|---|---|---|
| 0176948 | 9/1985 | European Pat. Off. . |
| 0411543 | 2/1991 | European Pat. Off. . |
| 2225065 | 5/1990 | United Kingdom . |
| WO82/00590 | 3/1982 | World Int. Prop. O. . |

Primary Examiner—Randall L. Green
Assistant Examiner—Mary Beth Jones
Attorney, Agent, or Firm—Frishauf, Holtz, Goodman & Woodward

[57] ABSTRACT

A transfusion pump 10 is that ① when the door 13 is opened to set the tube, the clamping member 53 is retained in engagement with the first unclamp retaining portion 61 by manual operation so as to be set at the unclamp position, ② when the door 13 is closed after the tube has been set, the clamping member 53 is released from its engagement with the first unclamp retaining portion 61 by the first unclamp releasing portion 63, and retained in engagement with the second unclamp retaining portion 64 so as to be set at the unclamp position, and ③ when the door 13 is opened after its closing, the clamping member 53 loses its engagement with the second unclamp retaining portion 64 so as to be set at the clamp position.

2 Claims, 6 Drawing Sheets

TRANSFUSION PUMP

BACKGROUND OF THE INVENTION

1. Field of the Invention

The present invention relates to a transfusion pump such as a peristaltic pump or roller pump to pump fluids such as liquid medicine.

2. The Prior Art

A conventional transfusion pump comprises a housing body, a door supported on the housing body for pivotal movement between an open position and a closed position, a tube pressing means disposed in the housing body, a platen disposed on the door so as to support a tube against the tube pressing motion of the tube pressing means when the door is closed, and a door locking member for locking the door to the housing body.

In this transfusion pump, an elastic tube is intermittently collapsed between the platen and the tube pressing means by means of the same tube pressing means, whereby a liquid in the tube is displaced and transported, while the tube is allowed to return to its original shape each time the pressing force applied thereon is released so as to expand the liquid passage. Thus, the pump can provide a pumping action.

By the way, a transfusion pump is used for the purpose of accurately feeding a small amount of transfusion liquid to the body of a patient, thereby ensuring the safety of the patient. Thus, it must be strictly prevented that the transfusion liquid is allowed to flow under no control, when the transfusion pump is used.

Figure 9:
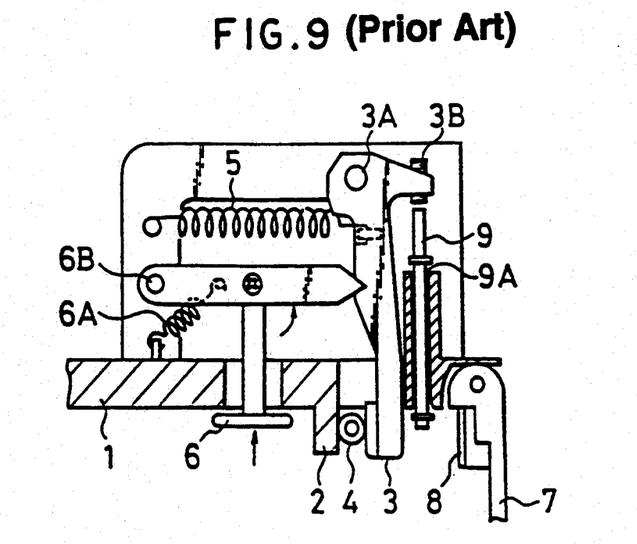
FIG. 9 is a tube clamp device of the convential peristaltic pump.

In a conventional transfusion pump, accordingly a tube clamp device as shown in FIG. 9 is used. The conventional tube clamp device comprises a tube receiving member 2 disposed on a housing body 1, a clamping member 3 disposed for rotation about a fulcrum 3A provided on the housing body 1, which can clamp a tube 4 between the tube receiving member 2 and the clamping member 3, an urging member 5 for urging the clamping member 3 toward the tube receiving member 2, a retaining lever 6 disposed on the housing body 1, which can retain the clamping member 3 in an unclamped position where the tube 4 is, an unclamped retaining portion 8 provided on a door 7, and a pin 9 inserted in a supporting hole 9A provided in the housing body 1, which is pushed by the unclamped retaining portion 8 of the door 7 when the door 7 is closed so as to retain the clamping member 3 in the unclamp position where the tube 4 is unclamped. In addition, the clamping member 3 is provided with an adjusting screw 3B at a portion thereof that collides the pin 9, and an urging member 6A is disposed between the housing body 1 and the retaining lever 6, which causes the retaining lever 6 to move from a position where it is engaged with the clamping member 3.

The tube clamp device which has the aforementioned constitution will be operated as described in the following items (1) to (3).

(1) When the door 7 is opened to set a tube 4 in the device, the retaining lever 6 is pushed to set the clamping member 3 at the unclamped position thereof. In this state, the retaining lever 6 rotates about the fulcrum 6B to engage its end with the concave part of the clamping member 3 so that the clamping member 3 is retained in the unclamped position.

(2) When a tube 4 is set in place and the door 7 is closed to start a transfusion of liquid, the unclamped retaining member 8 of the door 7 pushes the pin 9 and this pin 9 further collides with the adjusting screw 3B of the clamping member 3 so that the clamping member 3 is moved in an unclamping direction.

After the clamping member 3 is further opened to the unclamping direction, the end of the retaining lever 6 and the concave part of the clamping member 3 are disengaged so that the retaining lever 6 is returned to a position where it is not engaged with the clamping member 3 by means of the urging member 6A.

As long as the door 7 is kept closed in this state, the clamping member 3 collides with the pin 9 so as to be continuously retained in the unclamped position, whereby the transfusion pump imparts the pumping action to the tube that is kept in the unclampled state, thus carrying out the transfusion of liquid.

(3) When the transfusing operation is finished and the door 7 is opened, the pin 9 which is pushed by the unclampled retaining portion 8 of the door 7, is released to move freely, whereby the clamping member 3 which has already disengaged with the retaining lever 6 clamps the tube 4 between the tube receiving member 2 and the clamping member 3 by virtue of the urging member 5, thus preventing the free flow of a transfusion liquid.

In this prior art, however, there are the following problems ① and ②.

① Movable members provided in the housing body 1 include the clamping member 3, retaining lever 6, pin 9 and other parts. The tube clamp device may, therefore, function improperly, and requires maintenance, because of the wear of these parts over time and the need to place chemical liquid on the supporting hole 9A for the pin 9.

② The position of the pin 9 which pushes the clamping member 3 when the door 7 is closed (the point where the clamping member 3 and the pin 9 collide with each other) is near the fulcrum 3A of the clamping member 3. The force of the unclamped retaining portion 8 of the door 7 pushing the pin 9, which overcomes the urging member 5 to press the clamping member 3 to the unclamping direction is therefore very large. This large force may cause bending the whole of the transfusion pump so that the transfusion pump as a whole may function improperly.

The present invention is intended to provide a compact tube clamp device when the tube clamp device is installed in a transfusion pump in order that a transfusion liquid is prevented from freely flowing therein. The clamp design prevents the tube clamp device from functioning improperly, and further prevents the transfusion pump as a whole from functioning improperly.

SUMMARY OF THE INVENTION

According to a first aspect of the present invention, there is provided a transfusion pump comprising a housing body, a door supported on the housing body for pivotal movement between an open position and a closed position, a tube pressing means disposed in the housing body, a plate-like receiving member disposed on the door so as to support a tube against the tube pressing motion of the tube pressing means when the door is closed, a door locking member for maintaining the door closed to the housing body, and a tube clamp device which unclamps the tube when the door is opened to set the tube, and continuously unclamps the tube when the door is closed after the tube has been set, and clamps the tube when the door is opened after it has previously been closed comprising: the tube clamp device has a tube receiving member disposed on the housing body; a clamping member disposed for movement on the housing body, which can clamp the tube between the tube receiving member and the clamping member; an urging member for urging the clamping member toward the tube receiving member; a first unclamped retaining portion disposed on the housing body; which can retain the clamping member at an unclamped position where the tube is unclamped when the door is opened; a first unclamped releasing portion disposed on the door, which collides with the projecting end of the clamping member on the door side when the door is closed, thereby releasing the engagement of the clamping member with the first unclamped retaining portion; and a second unclamped retaining portion disposed on the door, which collides with the projecting portion of the clamping member on the door side, whose engagement with the first unclamped releasing portion has been previously released by the first unclamped releasing portion when the door is closed, thereby retaining the clamping member in engagement therewith so that the clamping member is continuously retained in the unclamped position where the tube is unclamped, wherein ① when the door is opened to set the tube, the clamping member is retained in engagement with the first unclamped retaining portion by a manual operation so as to be set at the unclamped position, ② when the door is closed after the tube has been set, the clamping member is released from engagement with the first unclamped retaining portion by the first unclamped releasing portion, and retained in engagement with the second unclamped retaining portion so as to be set at the unclamped position, and ③ when the door is opened after having been closed previously the clamping member loses its engagement with the second unclamped retaining portion so as to be set at the clamped position.

According to a second aspect of the present invention, there is provided a transfusion pump in which the clamping member is adapted to be urged to such a direction that it is engaged with the first unclamped retaining portion when the clamping member is moved from the clamped position to the unclamping direction by manual operation.

The term "clamped" used here means to interrupt the passage of a liquid in a tube by pressing the tube, and "unclamped" means a state in which the liquid is permitted to flow by releasing the pressing of the tube.

According to the first aspect of the present invention, there will be obtained the following effects ① and ②.

① The tube clamp device only has the clamping member as a movable member provided in the housing body. It is therefore possible to make compact the constitution of the device with a small number of parts and to prevent any improper function of the tube clamp device which may be caused by the wear of parts with time or the deposition of any chemical liquid in the tube clamp.

② The second unclamp retaining portion which retains the clamping member in the unclamped position against the urging member when the door is closed, is a part which collides with the projecting end of the clamping member on the door side, and the force of the second unclamped retaining portion, which overcomes the urging member to push the clamping member in an unclamping direction is, therefore, relatively small. As a result, it is possible to prevent the transfusion pump as a whole from functioning improperly, because this force does not bend the transfusion pump as a whole.

According to the second aspect of the present invention, there will be also obtained the following effect ③.

③ The clamping member engages with the first unclamped retaining portion when operated by hand. It is therefore possible to make compact the constitution of the device, without injuring its operability.

DETAILED DESCRIPTION

Referring to FIG. 1 and FIGS. 6 to 8, a peristaltic pump 10 has a housing 11 and a door 13 supported on the housing 11 through a door shaft 12 for pivotal movement between an open position and a closed position. The door 13 is provided with a knob 14 which can be rotated to lock the door 13 in the closed position and to unlock the door.

Figure 1:
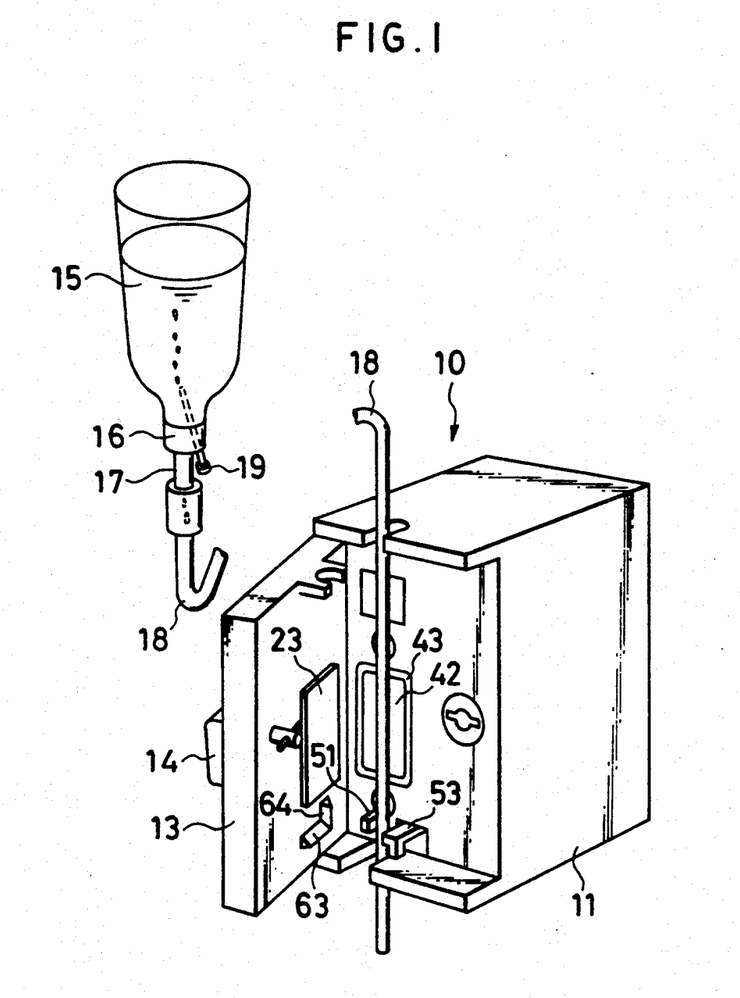
FIG. 1 is a schematic view showing a peristaltic pump as one embodiment of the present invention.

The pump 10 is capable of effecting a pumping action on an intermediate portion of a tube 18 which is connected to a liquid guide needle 17 piercing a stop cock 16 of a transfusion vessel 15 shown in FIG. 1, so as to transfuse a liquid from the transfusion vessel 15 into the body of a patient. Numeral 19 denotes a ventilation needle.

Figure 6A:
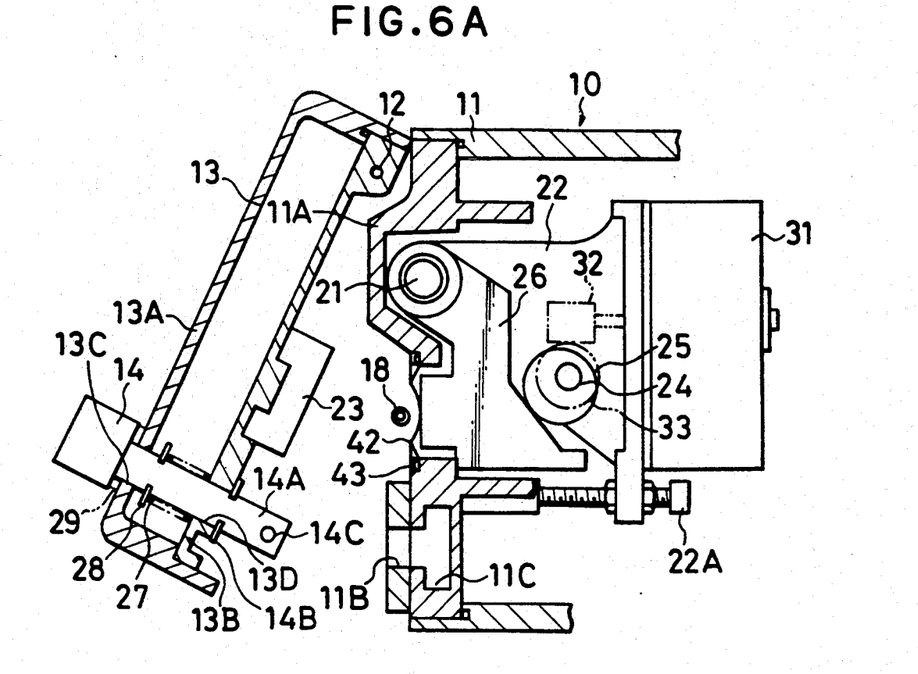
Figure 6B:
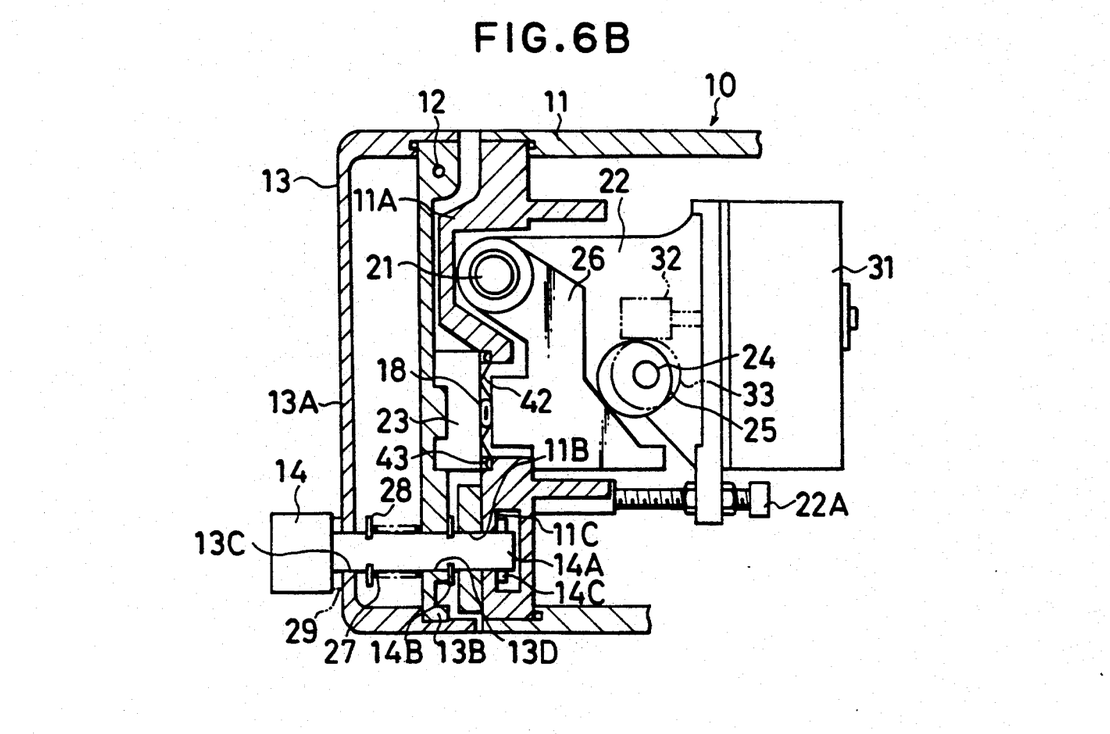
Figure 7:
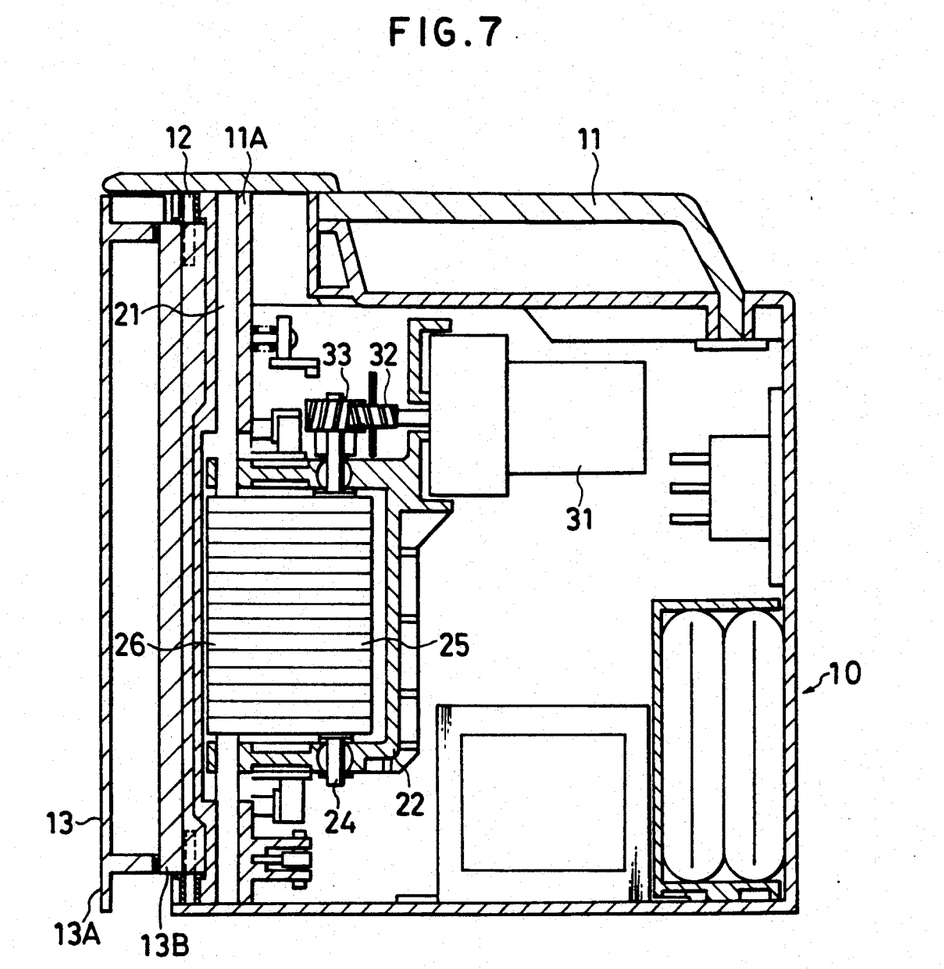
FIG. 7 is a vertical cross-sectional view showing the peristaltic pump.
Figure 8:
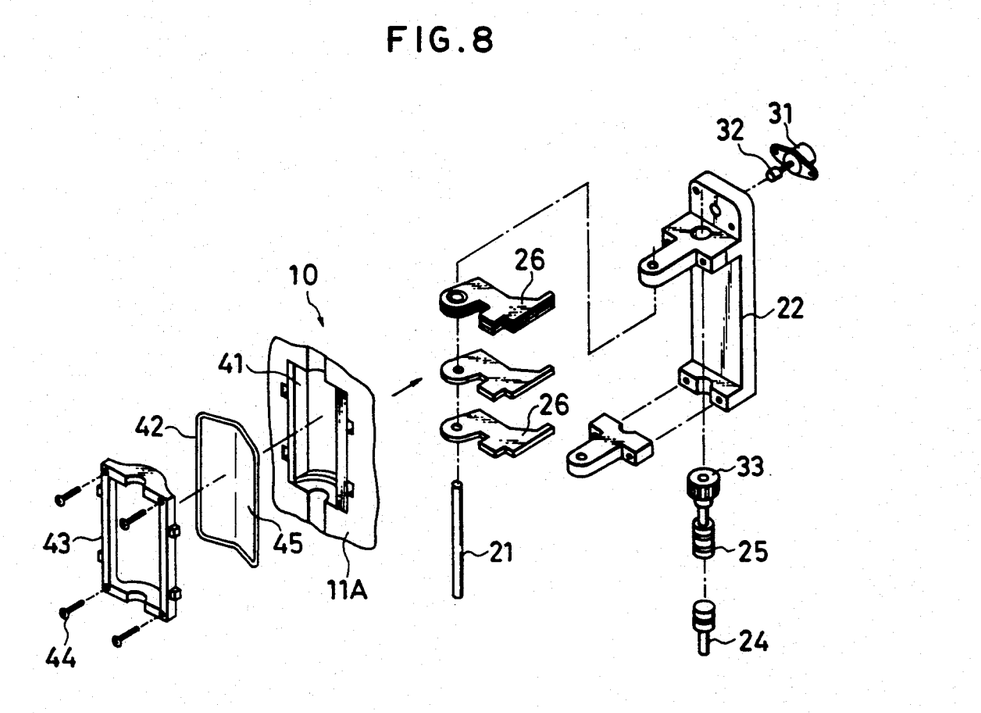
FIG. 8 is an exploded perspective view showing a critical portion of the peristaltic pump.

As shown in FIGS. 6 to 8, the pump 10 has a supporting member 22 carried on a bracket 11A fixed to the housing 11 through a pivot shaft 21. The supporting member 22 is supported for rotation about the pivot shaft 21 and it will be fixed on the bracket 11A at a predetermined rotative position about the pivot shaft 21 by a fixing screw 22A. The fixing screw 22A enables the supporting member 22 to be adjustable in its fixed position so that when each of eccentric cams 25 mentioned below actuates a finger group 26A toward the plate-like receiving member 23, each finger 26 is set at a collapse position where the tube is properly collapsed.

On the other hand, the door 13 of the pump 10 comprises a combination of a cover plate 13A and a back plate 13B, and the back plate 13B has a plate-like receiving member 23 fixed thereon.

The supporting member 22 has a cam shaft 24 arranged in parallel to the pivot shaft 21, wherein a plurality of cams 25 are incorporated in the longitudinal direction of this cam shaft 24 so as to be fixedly provided thereon, and a plurality of fingers 26 are incorporated, each of which is rockable about the pivot shaft 21 and pressed by each cam 25.

In this state, each finger 26 is adapted to be actuated by a corresponding eccentric cam 25 between a retracted position and an operative position. When the door 13 is closed, the plate-like receiving member 23 can be located so as to oppose the group of fingers 26A, thereby carrying the tube 18 which is disposed between the plate-like receiving member 23 and the fingers 26. The fingers are successively set to the operative position by the operation of the successive eccentric cams 25 so that the position where the tube 18 is collapsed by the fingers is progressively moved in the longitudinal direction of the tube. It is to be noted that the tube is normally closed by at least one finger 26. The arrangement is such that, when one of the fingers 26 has commenced its backward movement beyond the maximum collapse position, the next finger keeps the tube in the pressed condition so as to keep the internal liquid passage of the tube 18 closed until the abovementioned finger 26 travels a distance large enough to open the portion of the internal liquid passage under this finger 26.

The knob 14 of the pump 10 keeps the door 13 closed to the housing 11, because it is composed as mentioned below. Namely, the knob 14 which has a knob shaft 14A running through holes 13C and 13D provided in the cover plate 13A and back plate 13B of the door 13, is fitted in the door 13 by a snap ring 14B provided on an intermediate portion of the knob shaft 14A projecting from the back plate 13B, and it has an engaging pin 14C provided at the projecting end of the knob shaft 14A. On the other hand, the bracket 11A of the housing 11 has a hole 11B, into which the knob shaft 14A of the knob 14 is permitted to enter when the door 13 is closed, and an engagement part 11C is provided deep in the hole 11B, with which the engaging pin 14C engages. Namely, the knob 14 is adapted to cause the end of the knob shaft 14A to enter into the hole 11B when the door 13 is closed as shown in FIG. 6(B) from the open position of FIG. 6(A), and then cause the engaging pin 14C to engage with the engagement part 11C by the rotation of the knob shaft 14A, thereby retaining the door 13 in the closed position. In addition, the engagement part 11C has an inclined cam-shaped engagement surface which engages with the engaging pin 14C so that the knob shaft 14A is drawn to the housing 11 with the rotation of the knob shaft 14A.

The knob 14 further has a coil spring 27 provided between the door 13 and the knob 14. Namely, the coil spring 27 is disposed about the knob shaft 14A and fitted between a snap ring 28 provided on an intermediate portion of the knob shaft 14A and the back plate 13B of the door 13.

When the knob 14 retains the door 13 in the closed position to the housing 11, the knob 14 is engaged with the bracket 11A of the housing 11, without moving toward the closing direction, so that the door 13 can be relatively moved in the opening direction to the knob 14 and housing 11, assuming that the coil spring 27 is deformed by compression. Namely, the coil spring 27 imparts an urging force in the closing direction to the door 13 when the door 13 is retained in the closed position by the knob 14, and allows the door 13 to move in the opening direction when the pressing force of the finger 26 which is given to the plate-like receiving member 23 by way of the tube 18 exceeds the aforesaid urging force.

The pump 10 also has a drive motor 31 fixed to the supporting member 22 and has an output shaft carrying a worm gear 32 meshing with a worm wheel 33 which is fixed to one end of the cam shaft 24.

The arrangement is such that the cam shaft 24 is rotatingly driven by the drive motor 31 so as to rotate the eccentric cam 25 thereby activating successive fingers 26, whereby a pumping action is performed as explained before.

The peristaltic pump 10 of the present invention has a tube guide device as will be understood from the following description.

Namely, as shown in FIG. 8, each bracket 11A on the housing 11 has a pressing window 41 and a plate-like guide member 42 for closing the pressing window 41. The guide member 42 is fastened to the bracket 11A by means of screws 44 through a frame member 43 which presses the outer peripheral portion of the guide member 42. As will be seen from FIGS. 6(A) and 6(B), the guide member 42 is provided with a tube guide groove 45 formed in the surface thereof which faces the plate-like receiving member 23 when the door 13 is locked in the close position on the housing 11 so as to set the tube 18. The guide member 42 is made of a soft elastic material so as not to impede the collapsing action of the finger 26 when the successive fingers are set to the operative position for collapsing the tube 18. Therefore, the tube 18 is received in and guided by the guide groove 45 of the guide member 42 so as to be correctly set without winding of the tube, in such a manner that successive tube sections of a predetermined length are correctly located in the pressing regions of the successive fingers. Consequently, the tube is stably collapsed by the successive fingers as these fingers are set to the operative position, whereby a higher precision of control of the liquid flow rate can be obtained.

As shown in FIGS. 1 to 5, the peristaltic pump 10 has a tube clamp device 50.

Figure 2:
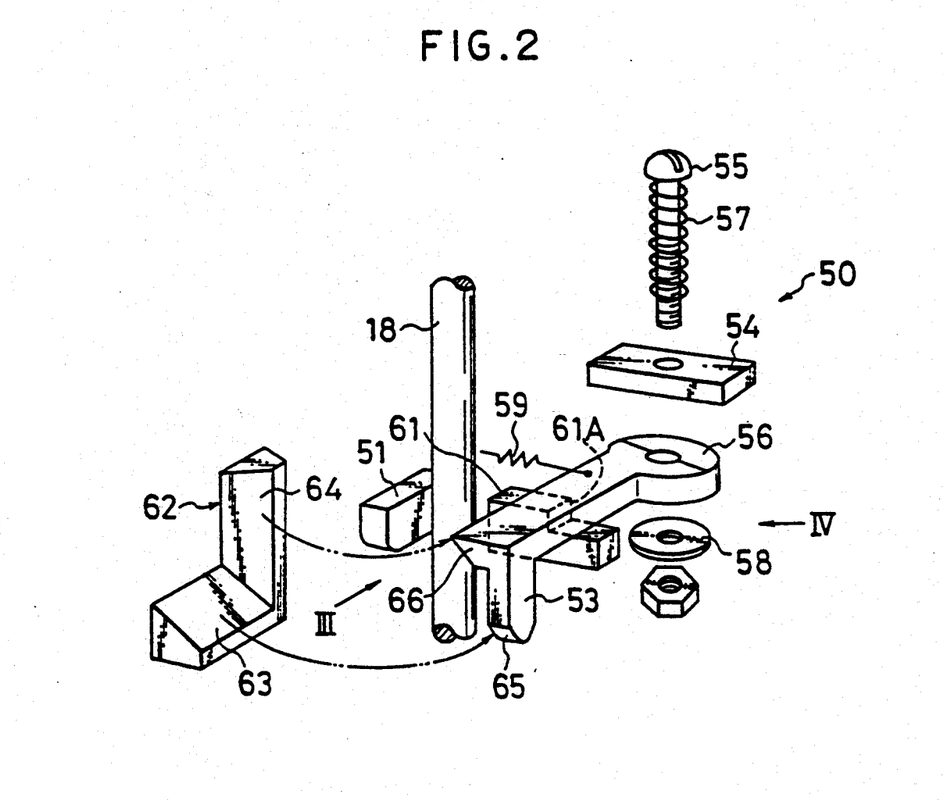
FIG. 2 is a schematic view showing a tube clamp device of the present invention.
Figure 3:
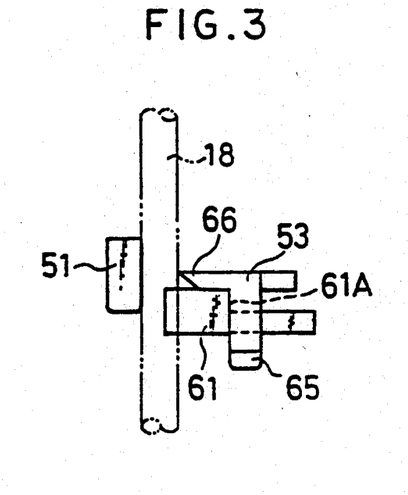
FIG. 3 is a partial schematic view of FIG. 2 taken in the direction of arrow III.
Figure 4:
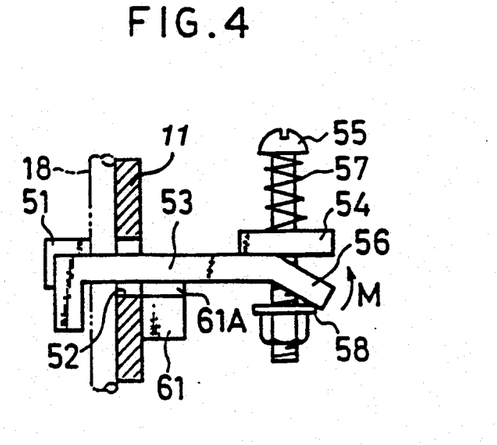
FIG. 4 is a partial schematic view of FIG. 2 taken in the direction of arrow IV, with a portion of the housing 11 shown in cross section.

Namely, the tube clamp device 50 has, under the guide member 42 on the housing 11, a tube receiving member 51 disposed so as to run along one side of the tube 18 which is fitted in the guide groove 45 and suspended therefrom and a clamping member 53 rockably contained in the housing 11, which can clamp the tube 18 between its end projected from the window portion 52 provided on the housing 11 and the tube receiving member 51.

The clamping member 53 is supported in the inside of the housing 11 so as to be rockable about a screw shaft 55 inserted in a fixing plate 54 provided on the housing 11. In this state, the clamping member 53 has a substantially half circumference of its base end about the screw shaft 55 which is provided as an inclined portion 56, and the base end including the inclined portion 56 is adapted to be held between a washer 58 provided on the screw shaft 55 which is urged upward by the urging member or a spring 57 and the said fixing plate 54. This arrangement is such that the clamping member 53 is given with such a moment of movement as shown by the designation M in FIG. 4 about its base end and is urged in a direction so that it engages with the first unclamped retaining portion 61 when it is rockingly actuated from the clamp position in the unclamping direction by manual operation, as described below.

The tube clamp device 50 has an urging member or a spring 59 for urging the clamping member 53 toward the tube receiving member 51, which is provided between the housing 11 and a longitudinally intermediate portion of the clamping member 53.

The tube clamp device 50 further has a stepped first unclamped retaining portion 61 disposed on the housing 11, which can be engaged with an intermediate portion of the clamping member 53 to retain the clamping member 53 in the position where the tube 18 is unclamped, when the door 13 is opened. The numeral 61A denotes a portion of the first unclamped retaining portion 61 which is engaged with the clamping member 53.

Furthermore, the tube clamp device 50 has, on a back plate 13B of the door 13, an L-shaped member 62 provided under the plate-like receiving member 23. The L-shaped member 62 is comprises of a first unclamped releasing portion 63 which is substantially wedge-shaped in cross section as its horizontal portion and a second unclamped retaining portion 64 which is also wedge-shaped in cross section as its vertical portion.

Figure 5:
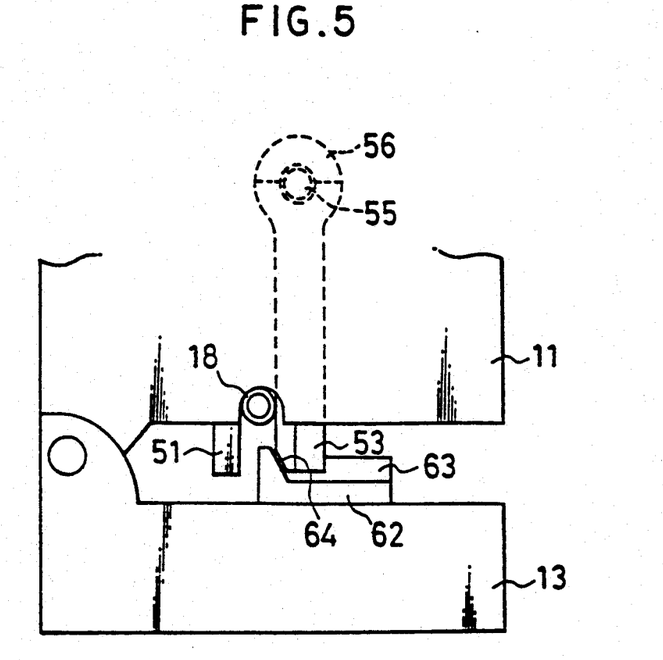
FIG. 5 is a schematic view showing the tube clamp device when a door is closed, FIG. 6(A) and (B) each is a transverse cross-sectional view showing the peristaltic pump.

The first unclamped releasing portion 63 is adapted to collide with the lower colliding surface 65 of the clamping member 53 at its projecting end on the door side to lift upward the clamping member 53 against the moment M of the said spring 57 when the door 13 is closed, whereby the clamping member 53 is automatically released from its engagement with the first unclamped retaining portion 61.

The second unclamped retaining portion 64 is adapted to collide with the side colliding surface 66 of the clamping member 53 at its projecting end on the door side to retain the clamping member 53 against the said spring 59 in engagement therewith when the door 13 is closed, whereby the clamping member 53 is retained in the position where the tube 18 is unclamped.

The operation of the peristaltic pump 10 will be described here.

(1) When the door 13 is opened to set a tube 18, the clamping member 53 is rockingly actuated from a clamped position in an unclamping direction by manual operation. In this state, the clamping member 53 is urged in a direction so that it is engaged with the first unclamped retaining portion 61 by the spring 57, and it is easily retained in engagement with the first unclamped retaining portion 61 so as to be set at the unclamped position. Thus, the tube 18 is fitted and set in the guide groove 45 of the guide member 42. In this state, the tube 18 is clamped and locked.

(2) When the door 13 is closed after the tube 18 has been set, the clamping member 53 is lifted up by the first unclamped releasing portion 63, interlocking with the closing motion of the door 13, so that its engagement with the first unclamped retaining portion 61 is released, while it is retained in engagement with the second unclamped retaining portion 64 so as to be still set in an unclamped position.

Since the tube 18 is held and locked between the fingers 26 of the peristaltic pump 10 and the plate-like receiving member 23 at that time, it is released from its clamping. Thus, the peristaltic pump 10 is brought into the state where its operation can be commenced.

After the operation of the peristaltic pump 10 is commenced, the tube collapsing position given by the respective fingers 26 which constitute the finger group 26A is caused to move in the longitudinal direction of the tube 18 by actuating each finger 26 by each cam 25, while the tube 18 is carried on the plate-like receiving member 23 fixed on the door 13. In this pump 10, accordingly, the elastic tube 18 is intermittently collapsed between the plate-like receiving member 23 and the tube pressing means by means of the same tube pressing means, whereby a liquid in the tube is displaced and transported, while the tube is allowed to resume its original shape when relieved from the pressing force applied thereon so as to expand the liquid passage, thus performing a pumping action. If any finger 26 of the finger group 26A collapses the tube excessively, an extraordinarily large elastic reaction force of the tube 18 will push back the door 13 in such a direction that it is alienated from the finger 26 against the urging force of the coil spring 27. By virtue of this arrangement, the plate-like receiving member 23 fixed to the door 13 is unburdened in such a direction that it is alienated from the finger 26, this is in a direction reverse to the tube collapsing direction, with the movement of the door 13, thereby absorbing an excessive portion of the tube collapsing force of the finger 26.

(3) When the door 13 is opened after the completion of the transfusing operation, the clamping member 53 loses its engagement with the second unclamped retaining portion 64 so as to be set at the clamped position, interlocking with the opening motion of the door 13. The arrangement is such that the clamping member 53 clamps the tube 18 between the tube receiving member 51 and the clamping member 53, thereby preventing the transfusion liquid from freely flowing.

(4) When the door 13 is closed to carry out the transfusing operation again after the door 13 has been opened to thereby interrupt the previous transfusing operation, the second unclamped retaining portion 64 resets the clamping member 53 interlocked with the closing motion of the door 13 so that it is pushed back to its unclamped position, whereby it becomes possible to carry out the transfusion of liquid.

According to the aforementioned embodiment, there will be obtained the following effects ① to ③.

① The tube clamp device 50 has only the clamping member 53 as any movable member provided on the housing 11. It is therefore possible to make the device compact device with a small number of parts and to prevent any improper function of the tube clamp device 50 which may be caused by the wear of parts with time or the deposition of any chemical liquid.

② The second unclamped retaining portion 64 which retains the clamping member 53 in an unclamped position against the spring 59 when the door 13 is closed, is a part which collides with the projecting end of the clamping member 53 on the door side, and the force of the second unclamped retaining portion 64 which overcomes the spring 59 to push the clamping member 53 in the unclamping direction is, therefore, relatively small. As a result, it is possible to prevent the transfusion pump 10 as a whole from functioning improperly, because this small force can not bend the entire pump 10.

③ The clamping member 53 engageable with the first unclamped retaining portion 61 when operated by hand. It is therefore possible to make compact the constitution of the device, without affecting its operability.

According to the present invention which has been described above, a compact tube clamp device can be provided when the tube clamp device is installed in a transfusion pump in order that a transfusion liquid is prevented from freely flowing therein, to prevent the tube clamp device from functioning improperly, and further to prevent the transfusion pump as a whole from functioning improperly.

What is claimed is:
1. A transfusion pump comprising:
a housing body;

a door pivotally mounted on said housing body, said door being pivotable between an open position and a closed position;

a tube pressing means provided in said housing body;

a plate-like receiving member mounted on said door which support a, said tube receiving an intermittent tube force from a tube pressing motion of said tube pressing means, when said door is moved to said closed position, thereby providing a pumping action;

a locking member in said housing body for keeping said door closed;

a tube clamp device that unclamps said tube when said door is open to enable an initial setting of said tube between said plate-like receiving member and said tube pressing means;

said tube clamp device maintaining said tube in an unclamped state when said door is closed after said tube has been initially set between said plate-like member and said tube pressing means;

said tube clamp device clamping said tube when said door is opened, after said door was closed after said initial setting of said tube;

said tube clamp device including:

a tube receiving member mounted in said housing body;

a clamping member movably positioned in said housing body, said clamping member being movable from a first position where said tube is unclamped to a second position where said tube is clamped, said clamping member when in said second position clamping said tube between said tube receiving member and said clamping member;

an urging member corrected to said clamping member for urging said clamping member toward said tube receiving member;

a first unclamped retaining portion mounted in said housing body which engages and retains said clamping member in said first position when said tube is not clamped, when said door is opened;

a first unclamped releasing portion mounted on said door, said first unclamped releasing portion colliding with a projecting portion of said clamping member on a side of said door that faces an interior portion of said housing body, when said door is closed, thereby releasing said clamping member from engagement with said first unclamped retaining portion;

a second unclamped retaining portion for engaging and retaining said clamping member, said second unclamped retaining portion being mounted on said door and colliding with said projecting portion of said clamping member on said side of said door, said clamping member being released from engagement with said first unclamped releasing portion by an operation of said first unclamped releasing portion when said door is closed, whereby said clamping member is retained in engagement with said second unclamped retaining portion so that said clamping member is retained in said first unclamped position when said tube is unclamped;

and wherein:

A. when said door is opened to enable said initial setting of said tube between said tube pressing means and said plate-like receiving member, said clamping member engages said first unclamped retaining portion by a manual operation of said clamping member so as to set said clamping member at said first position, thereby enabling a fluid to flow through said tube;

B. when said door is closed, after said tube has been initially set, said clamping member is released from engagement with said first unclamped retaining portion by said first unclamped releasing portion while said clamping member is retained in engagement with said second unclamped retaining portion so as to set said clamping member at said first position to enable said fluid to flow through said tube; and C. when said door is opened, after having been closed after said tube has been initially set between said tube pressing means and said plate-like receiving member, said clamping member disengages from said second unclamped retaining portion and is set at said second position to thereby clamp said tube to prevent said fluid flow through said tube.

2. The transfusion pump according to claim 1, further comprising:

urging means for urging said clamping member in a direction such that said clamping member engages with said first unclamped retaining portion when said clamping member is moved from said second position in a direction toward said first position to unclamp said tube by a manual operation of said clamping member.

* * * * *